US011510646B2

(12) United States Patent
Jensen et al.

(10) Patent No.: US 11,510,646 B2
(45) Date of Patent: Nov. 29, 2022

(54) ULTRASOUND IMAGING SYSTEM PROBE CABLE AND CONNECTOR

(71) Applicant: B-K Medical Aps, Herlev (DK)

(72) Inventors: Henrik Jensen, Nordhavn (DK); Robert Harold Owen, Stenlose (DK); Soren Juel Andersen, Copenhagen (DK); Christopher Beers, State College, PA (US); Niels Christian Sasady, Frederiksberg (DK); Per Ehrenreich Nygaard, Soeberg (DK)

(73) Assignee: BK MEDICAL APS, Herlev (DK)

( * ) Notice: Subject to any disclaimer, the term of this patent is extended or adjusted under 35 U.S.C. 154(b) by 874 days.

(21) Appl. No.: 15/479,818

(22) Filed: Apr. 5, 2017

(65) Prior Publication Data

US 2018/0289357 A1 Oct. 11, 2018

(51) Int. Cl.
| | | |
|---|---|---|
| *A61B 8/00* | (2006.01) | |
| *A61B 8/12* | (2006.01) | |
| *A61B 1/313* | (2006.01) | |
| *A61B 5/06* | (2006.01) | |
| *A61B 5/0215* | (2006.01) | |
| *A61B 8/14* | (2006.01) | |

(52) U.S. Cl.
CPC .......... *A61B 8/4444* (2013.01); *A61B 1/3132* (2013.01); *A61B 5/0215* (2013.01); *A61B 5/062* (2013.01); *A61B 8/12* (2013.01); *A61B 8/4254* (2013.01); *A61B 8/14* (2013.01); *A61B 8/4483* (2013.01); *A61B 8/461* (2013.01)

(58) Field of Classification Search
CPC ....... A61B 8/4444; A61B 8/4254; A61B 8/12; A61B 8/4483; A61B 5/062; A61B 1/3132
See application file for complete search history.

(56) References Cited

U.S. PATENT DOCUMENTS 6,325,674 B1 * 12/2001 Oliphant ................ H01R 24/62
439/329
6,398,775 B1 * 6/2002 Perkins ............. A61M 16/0486
604/514

(Continued)

FOREIGN PATENT DOCUMENTS

CN 101095613 A * 1/2008 ............... A61B 8/12
EP 1839559 A1 * 10/2007 ......... G02B 23/2484

*Primary Examiner* — Rochelle D Turchen
(74) *Attorney, Agent, or Firm* — Daugherty & Del Zoppo, Co. LPA

(57) ABSTRACT

An ultrasound probe includes a housing. The housing includes a first end, which internally houses: a transducer array and a tracking sensor, and a second end. The housing further includes a second portion extending between the first and second ends. The second portion houses: a first electrically conductive path extending from the transducer array through the second portion to the second end, which is opposite the first end, and a second electrically conductive path extending from the tracking sensor through the second portion to the second end. The probe further includes a single electro-mechanical connector with a physical interface configured to transfer signals carried by the first and second electrically conductive members off the probe. The probe further includes a single cable that routes the first and second electrically conductive members from the second end to the electro-mechanical connector.

18 Claims, 5 Drawing Sheets

(56) References Cited

U.S. PATENT DOCUMENTS

| | | | | |
|---|---|---|---|---|
| 6,547,788 B1 * | 4/2003 | Maguire | ............... | A61B 18/00 |
| | | | | 606/41 |
| 2002/0143275 A1 * | 10/2002 | Sarvazyan | ............. | A61B 5/036 |
| | | | | 600/587 |
| 2004/0267480 A1 * | 12/2004 | Day | ............... | G01R 31/318555 |
| | | | | 702/117 |
| 2013/0281819 A1 * | 10/2013 | Schmid | ............... | A61B 5/0095 |
| | | | | 600/407 |
| 2013/0338505 A1 * | 12/2013 | Schneider | ................ | A61B 8/12 |
| | | | | 600/444 |
| 2014/0031694 A1 * | 1/2014 | Solek | ................... | A61B 8/4494 |
| | | | | 600/459 |
| 2014/0133269 A1 * | 5/2014 | Hansen | ............. | A61B 1/00078 |
| | | | | 367/7 |
| 2015/0025390 A1 * | 1/2015 | Hewitt | ................ | A61B 8/4411 |
| | | | | 600/472 |
| 2016/0266069 A1 * | 9/2016 | Jenkins | ................ | G01N 29/043 |

* cited by examiner

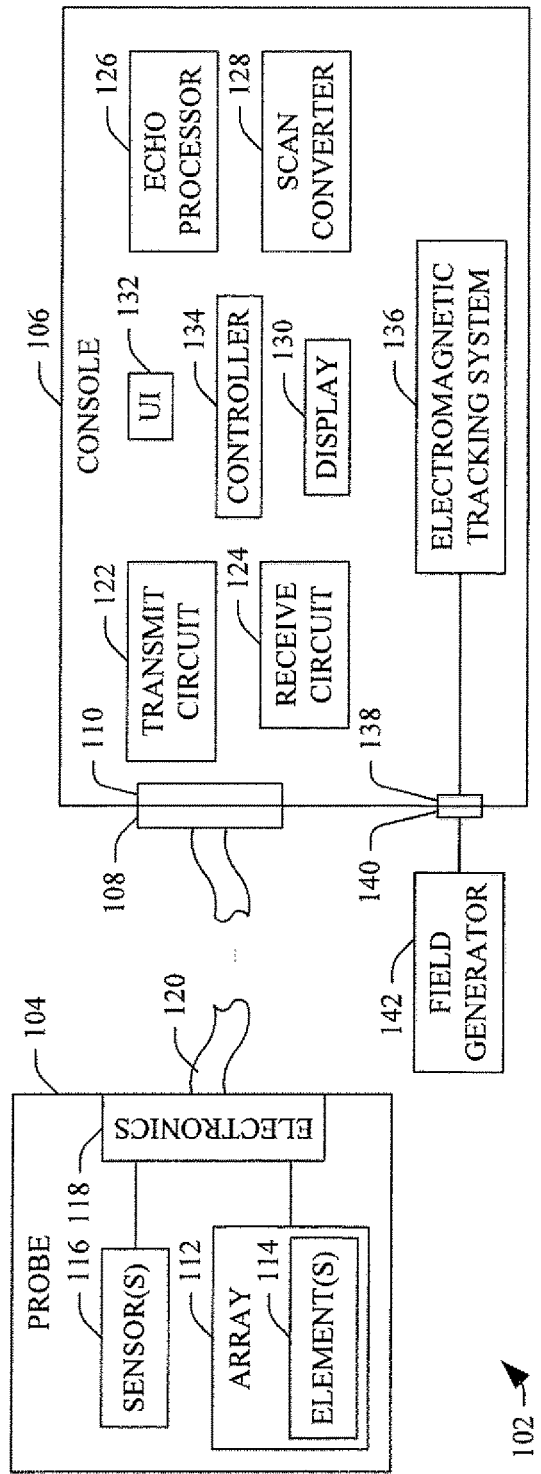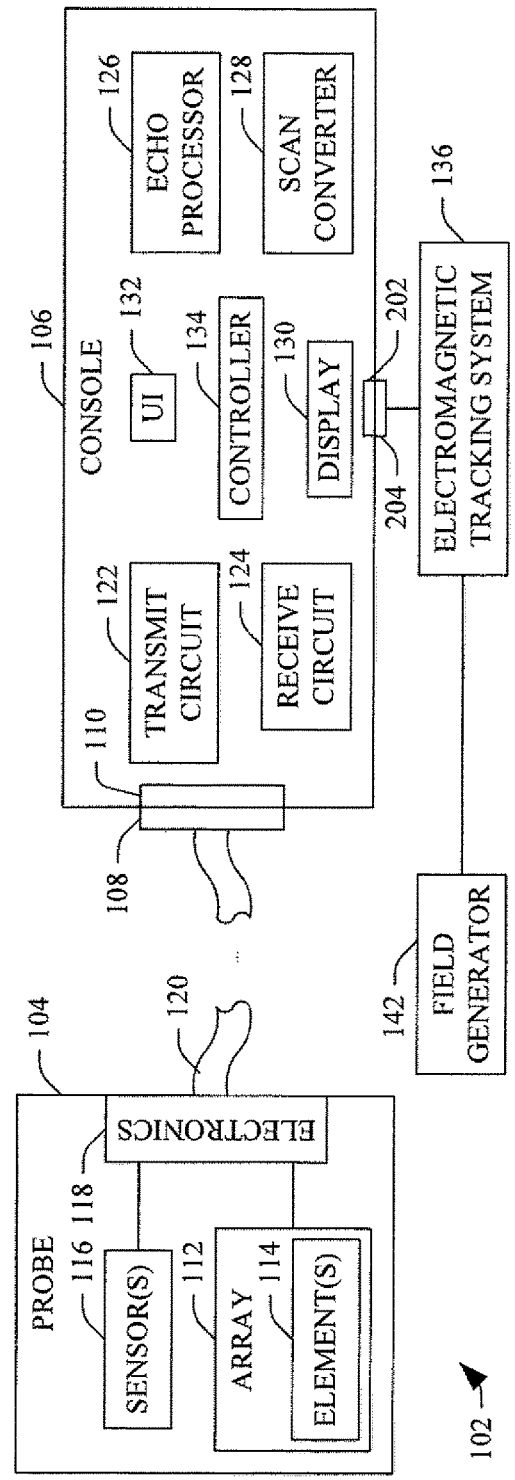

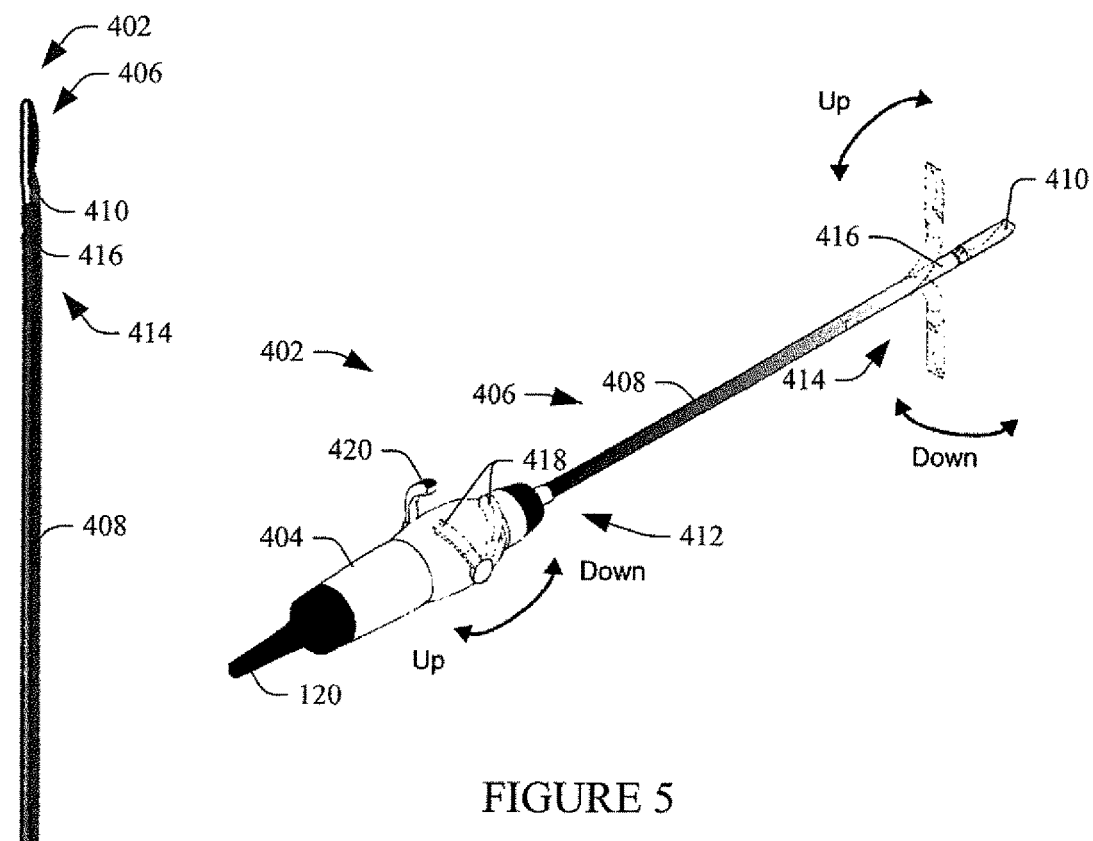
FIGURE 5
FIGURE 4
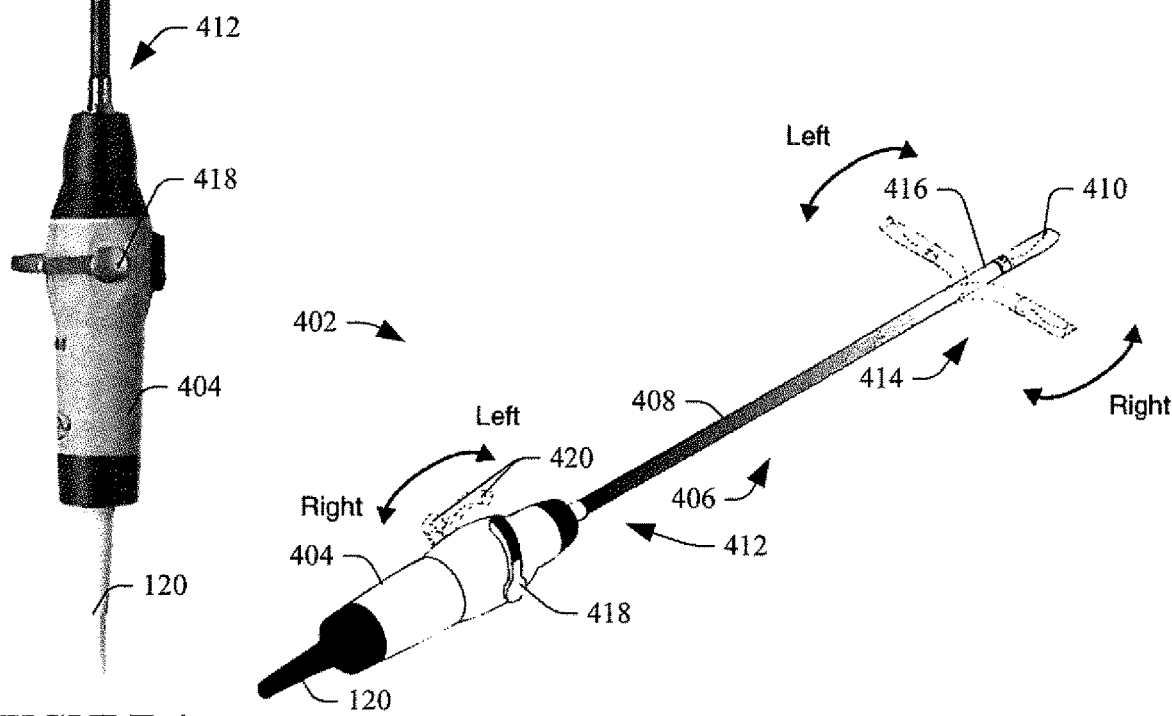
FIGURE 6

ULTRASOUND IMAGING SYSTEM PROBE CABLE AND CONNECTOR

TECHNICAL FIELD

The following generally relates to ultrasound imaging and more particularly to an ultrasound imaging system probe with a single cable and a single connector configured to transfer both an electrical signal indicative of a received echo and a tracking signal.

BACKGROUND

An ultrasound imaging system has included an ultrasound probe with a transducer array and a console. The ultrasound probe houses the transducer array, and the console includes a display monitor and a user interface. The transducer array transmits an ultrasound signal and receives echoes produced in response to the signal interacting with structure. The echoes are converted to electrical signals by the transducer array and are conveyed to the console. The electrical signals are routed via wires from the transducer array through a cable to an electromechanical connector electrically and mechanically connected to a complementary electromechanical connector of the console.

With some applications, a separate tracking system is used to spatially track the probe. A typical electromagnetic tracking system includes of a control unit, a field generator, and a sensor(s), which is affixed to the probe. The control unit processes the signal to the field generator and the signal from the sensor(s) to determine a spatial position of the sensor(s) relative to the field generator. In one system, the tracking sensor is temporarily attached on an outside of the probe via a click-on bracket or tape. However, the click-on sensor may be cumbersome to clean and/or in the way of a needle guide and/or a sterile cover.

Furthermore, there are now two cables to manage (one for the array and one for the tracking sensor), and the cables, the sensor, and the click-on bracket consume space. Furthermore, the measurement may be imprecise as the sensor may have to be placed some distance from the active part of the ultrasound transducer, which generally is what it is desired to be tracked. Generally, using a tracking system with an ultrasound system adds the complexity of attaching sensors to the ultrasound probe, connecting the sensor, connecting the magnetic field generator, interconnecting the tracking and the ultrasound system, configuring system, calibration or registration, etc.

SUMMARY

Aspects of the application address the above matters, and others.

In one aspect, an ultrasound probe includes a housing. The housing includes a first end, which internally houses: a transducer array and a tracking sensor, and a second end. The housing further includes a second portion extending between the first and second ends. The second portion houses: a first electrically conductive path extending from the transducer array through the second portion to the second end, which is opposite the first end, and a second electrically conductive path extending from the tracking sensor through the second portion to the second end. The probe further includes a single electro-mechanical connector with a physical interface configured to transfer signals carried by the first and second electrically conductive members off the probe. The probe further includes a single cable that routes the first and second electrically conductive members from the second end to the electro-mechanical connector.

In another aspect, a probe including an elongate shaft with first and second ends, and a head disposed at one of the first or second ends, wherein the head encloses a transducer array and a tracking sensor. The probe further includes a handle disposed at the other of the first or second ends. The probe further includes a single cable extending from the handle to a single connector of the single cable. The probe further includes first and second electrically conductive elements extending inside of the head, the shaft, the handle, the single cable and the single connector, respectively from the transducer array and the tracking sensor to a circuit board disposed inside of the single connector.

In another aspect, a method includes transmitting, with a transducer array of a probe, an ultrasound signal in response to a transmit pulse. The method further includes receiving, with the transducer array, an echo signal produced in response to an interaction of the ultrasound signal with structure, and generating, with the transducer array, an electrical signal indicative of the receive echo signal. The method further includes routing, via a first electrically conductive pathway inside of the probe, the electrical signal from the transducer array to a readout connector of a cable of the probe, and routing, via a second electrically conductive pathway inside of the probe, a tracking signal from a tracking sensor proximate to the transducer array to the same readout connector inside of the same cable of the probe. The method further includes transferring the electrical signal and the tracking signal off the probe through the same readout connector.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIG. 1 schematically illustrates an example ultrasound imaging system with an integrated tracking system and a probe with an integrated tracking sensor where a transducer array and the tracking sensor of the probe are connected to a console via a single cable and a single cable connector;

FIG. 2 schematically illustrates a variation of FIG. 1 in which the tracking system is located external from the console;

FIG. 4 illustrates a side view of an example laparoscopic probe;

FIG. 5 schematically illustrates a perspective view of the probe of FIG. 4 showing up/down articulation of a head of the probe;

FIG. 6 schematically illustrates a perspective view of the probe of FIG. 4 showing right/left articulation of a head of the probe;

DETAILED DESCRIPTION

Figure 3:
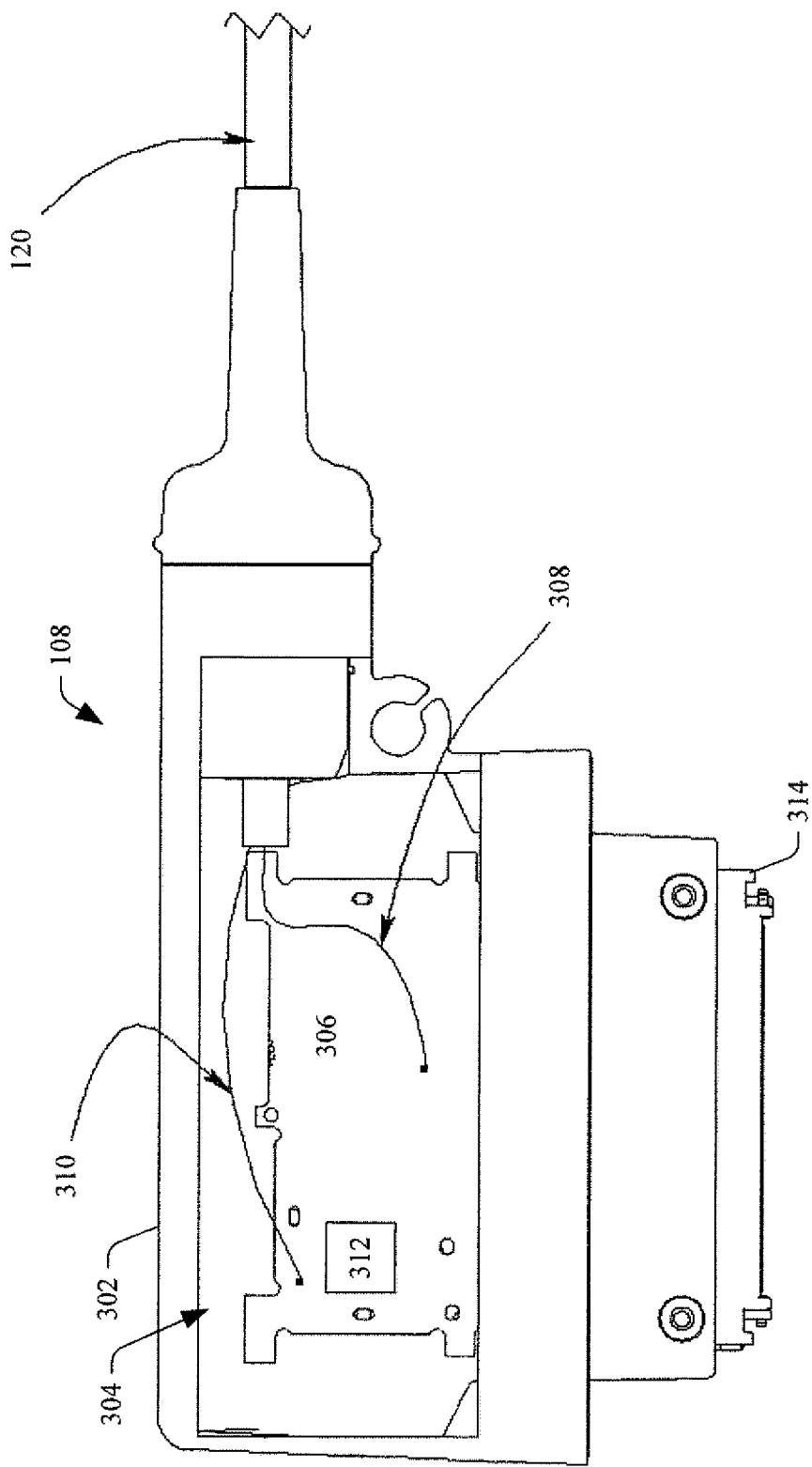
FIG. 3 illustrates an example of the single cable connector.

FIG. 1 schematically illustrates an imaging system 102 such as ultrasound imaging system. The imaging system 102 includes an ultrasound probe 104 and a console 106.

In general, the probe 104 can be any type of ultrasound imaging probe. For explanatory purposes and sake of brevity and clarity, the probe 104 is described with particular application to laparoscopic and endocavitary ultrasound imaging probes. However, it is to be understood that the probe 104 is not limited to laparoscopic and/or endocavitary ultrasound imaging probes, or the laparoscopic and/or endocavitary ultrasound imaging probes described herein. Non-limiting examples of ultrasound applications include image fusion (e.g., ultrasound and magnetic resonance (MR)), instrument (e.g., biopsy needle, ablation device, etc.) tracking, and/or other ultrasound applications.

The ultrasound probe 104 includes a transducer array 112 with a transducer element(s) 114, a tracking (electro-magnetic) sensor(s) 116, and electronics 118. The tracking sensor(s) 116 is integrated inside of the probe 104. In one instance, the tracking sensor(s) 116 is integrated and/or disposed in the probe 104 proximate of the transducer element(s) 114. In another instance, the tracking sensor(s) 116 is disposed in the probe 104 distal to the transducer element(s) 114. Integrating the tracking sensor(s) 116 in the probe 104 as such, in one instance, can eliminate a need for a click-on bracket and/or other mechanism for attaching the tracking sensor(s) 116 on the outside of the probe 104.

The electronics 118 receives and routes signals from the transducer element(s) 114 and from the tracking sensor(s) 116 (analog signals or digitized versions thereof) to wires (not visible) of a same single cable 120 that terminate at a circuit board (not visible) in a same single electro-mechanical connector 108 at an end of the cable 120. In one instance, routing the signals in the same cable 120 may improve cable management and/or make it easier to clean relative to a configuration with separate cables. As described in greater detail below, the signals from the transducer element(s) 114 and the tracking sensor(s) 116 (the analog or the digitized signals) are transferred off the probe 104 via the same single electro-mechanical connector 108.

The console 106 includes a complementary electro-mechanical connector 110. For example, in one instance the connectors 108 and 110 are configured as plug and socket connectors, where the connector 108 has a "male" configuration and is a plug with electrically conductive pins or prongs, and the complementary connector 110 has a "female" configuration and is a mating receptacle with electrically conductive sockets configured to receive the pins or prongs. Mechanically engaging the connectors 108 and 110 places the pins/prongs and sockets in electrical communication. Other configurations are also contemplated herein. The signals are conveyed from the probe 104 to the console 106 via the connectors 108 and 110.

The console 106 further includes a transmit circuit 122 and a receive circuit 124. The transmit circuit 122 transmits a control signal(s), via the cable 120 and to the probe 104, that excites one or more of the transducer element(s) 114 of the transducer array 112, which causes the transducer element(s) 114 to transmit an ultrasound signal or pressure wave. The receive circuit 124 receives, via the cable 120, the electrical signals produced by the element(s) 114 of the transducer array 112, which are indicative of the echoes received by the element(s) 114 of the transducer array 112.

The console 106 further includes an echo processor 126 that processes the received electrical signals. With B-mode imaging, such processing includes beamforming such as delay and sum beamforming of the electrical signals, which produce a sequence of focused, coherent echo samples along focused scanlines of a scanplane. Other processing may process the electrical signal for A-mode, C-plane, Doppler, etc. applications. Other processing may lower speckle, improve specular reflector delineation, and/or includes FIR filtering, IIR filtering, etc. The signals can first be amplified and/or otherwise pre-processed and/or conditioned.

The console 106 further includes a scan converter 128 that scan converts frames of data to generate data for a display 130. The console 106 further includes a user interface (UI) 132 with one or more input devices (e.g., a button, a knob, a touchscreen, etc.) and/or one or more output devices (e.g., a display monitor, an audio presenter, etc.), which allows for interaction with the system 102. The console 106 further includes a controller 134 that controls at least one of the transmit circuit 122, the receive circuit 124, the echo processor 126, the scan converter 128, the display 130 and/or the user interface 132.

The console 106 further includes an integrated electromagnetic tracking system 136 and an electro-mechanical interface 138 configured to mechanically engage and electrically communicate with a complementary electro-mechanical interface 140 of a field generator 142, which is external to the console 106. The interfaces 138 and 140 can be electro-mechanical connectors as described herein and/or otherwise. The controller 134 synchronizes the processing of the signals from the tracking sensor(s) 116 and the generating the electro-magnetic field by the field generator 142. An example electromagnetic tracking system is the Aurora tracking system, a product of NDI, which is headquartered in Ontario, Canada.

FIG. 2 shows a variation of the configuration shown in FIG. 1 in which the electromagnetic tracking system 136 is external to the console 106. In this variation, the console 106 includes an electro-mechanical interface 202 configured to mechanically engage and electrically communicate with a complementary electro-mechanical interface 204 of the electromagnetic tracking system 136. The electromagnetic tracking system 136, similar to FIG. 1, controls the field generator 142, which is external to the console 106. The interfaces 138 and 140 can be electro-mechanical connectors as described herein and/or otherwise.

FIG. 3 schematically illustrates an example of the electro-mechanical connector 108 of the probe 104.

The illustrated connector 108 includes a housing 302. A region 304 of the housing 302 is shown transparent so that a portion of an inside of the probe 104 is visible in the drawing. The connector 108 further includes a circuit board(s) 306. A first set of wires 308 from the cable 120 routes signals between the circuit board(s) 306 and the console 106. A second set of wires 310 from the same cable 120 routes signals between the same circuit board(s) 306 and the console 106. In the illustrated embodiment, circuitry 312 converts analog signals from the tracking sensor(s) 116 to digital signals. In one instance, the conversion includes reducing the amount of data and converting the signals to coordinates, which mitigates transmitting sensor signals across the connectors 108 and 110.

The circuit board(s) 306 routes the signals from the transducer array 112 and the digitized tracking sensor signals to pins or sockets (not visible) recessed within a portion 314 of the connector 108, which is configured to mechanically engage a complementary portion of the complementary electro-mechanical connector 110 of the console (FIGS. 1 and 2). The circuit board(s) 306 also routes control, power, etc. signals from the complementary electro-mechanical connector 110 of the console (FIGS. 1 and 2) received by the pins or sockets (not visible) recessed within the portion 314 to the first and second sets of wires 308 and 310.

In this example, signals are transferred from the circuit board(s) 306 over a bus, such as the serial peripheral interface (SPI) bus or other synchronous serial communication interface. In one instance, the circuitry 312 includes hardware built around the SPI bus. This hardware provides gating controlled by a pair of differential signals. The gating, in one instance, mitigates noise during receive and/or mitigates disturbances in the transmit pulse during transmit. In this example, the communications link triggers with a 5-15 MHz clock, such as a 10 MHz clock, and operates through cycles of Transmit (TX), Receive (RX), and Communicate operations, using the same channels or electrodes of the connectors 108 and 110. Table 1 describes an example configuration of the pinout of the connector 108.

TABLE 1

Example configuration of the pinout.

| Pin(s) | Name | Description |
|---|---|---|
| D3 | +5$V_D$ | +5V supply for the digital circuitry (probe control logic) referenced to noisy ground. |
| D4 | SafeGate− | Differential signal to gate single ended control signals during the transmit pulse and receive period. |
| D5 | SafeGate+ | |
| C4 | S_SCK | SPI data clock from master. |
| C5 | S_SS− | SPI device select enable signal. Active low. |
| D1 | S_MOSI | SPI Master Output, Slave data Input signal line. Data to slave from master. |
| D2 | S_MISO | SPI Master Input, Slave data Output signal line. Data from slave to master. |
| C3 | INT− | Active low interrupt signal from the probe to the console to indicate that data is available on the SPI bus. This signal has a strong pull-up on the console side. |

A size of the circuit board(s) 306 is such that it fits within a same housing of a probe not including the circuit board(s) 306. That is, the footprint of the probe 104 does not change. Furthermore, the connector 108 does not require any modification to the pinout relative to a probe not including the circuit board(s) 306, and the connector 110 does not require any modification to transfer data between the probe 104 and the console 106. The circuit board(s) 306, in the configuration described herein, includes the circuitry 312 for controlling data transfer (e.g., the TX, RX, and communicate cycle), digitizes the tracking signal (for configurations which digitize the tracking signal), and supplies power for the tracking sensor 116, etc.

Figure 7:
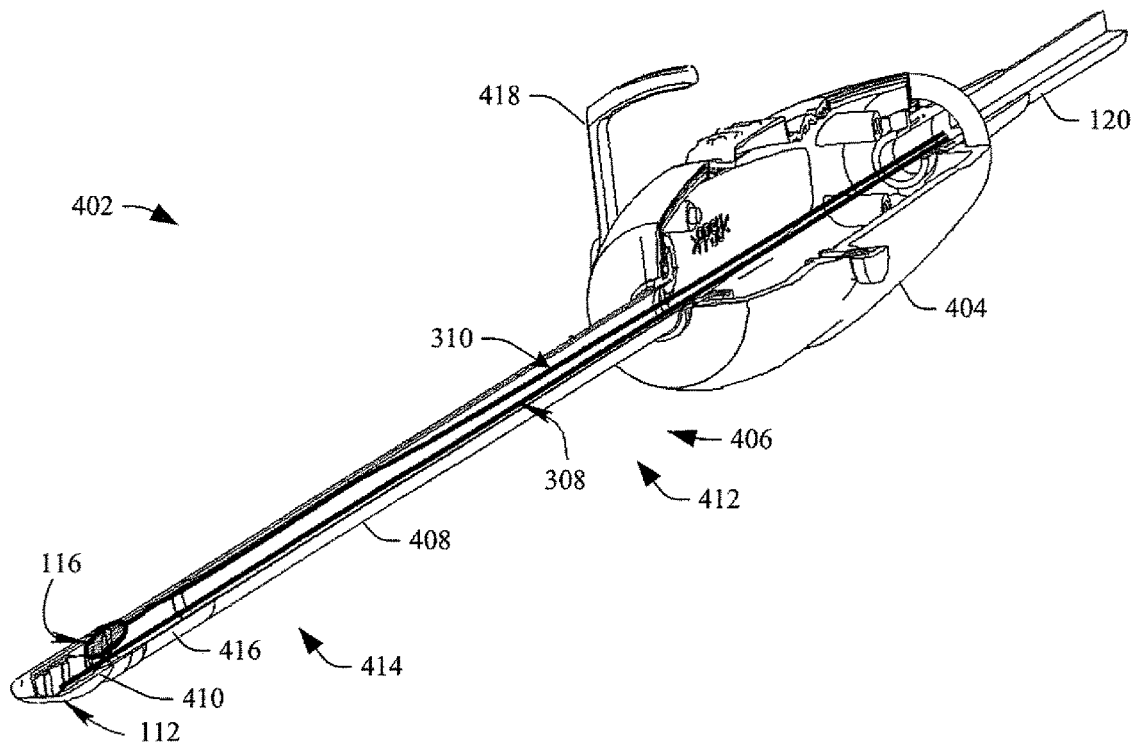
FIG. 7 illustrates example of the probe of FIG. 4 with a cut-away showing example sensor placement and routing of a wire therefrom to the cable.
Figure 8:
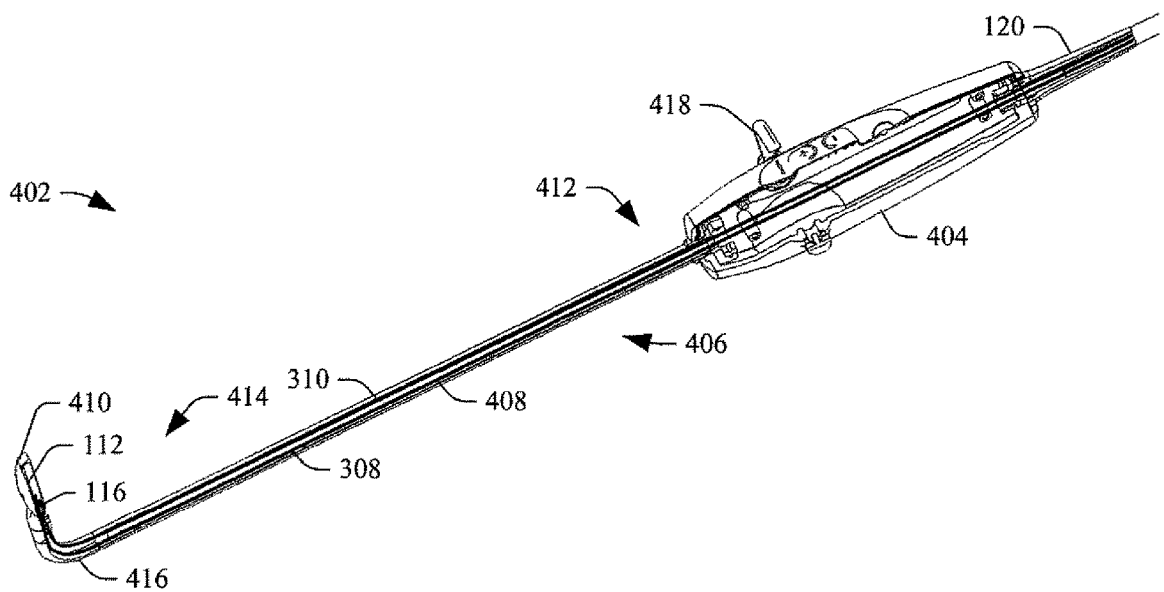
FIG. 8 illustrates the probe of FIG. 7 with the tip articulated.

FIGS. 4, 5, 6, 7 and 8 illustrate an example of the probe 104. FIG. 4 illustrates a side view of the probe 104. FIG. 5 illustrates a perspective view of the probe 104 showing up and down articulation. FIG. 6 illustrates a perspective view of the probe 104 showing right and left articulation. FIG. 7 schematically illustrates a perspective view of a non-articulated probe 104 with a cut-out showing a portion of an inside of the probe 104. FIG. 8 schematically illustrates a perspective view of an articulated probe 104 with a cut-out showing a portion of an inside of the probe 104. In FIGS. 4, 5, 6, 7 and 8, the probe 104 is configured as a laparoscopic probe 402.

With reference to FIGS. 4, 5, 6, 7 and 8, the laparoscopic probe 402 includes a handle 404 and an elongate shaft 406 having a long axis. The elongate shaft 406 includes a body 408 and a head 410, both aligned along the long axis. The body 408 includes a first end 412 and a second opposing end 414. The first end 412 of the body is affixed to the handle 404. An articulating member 416 couples the second end 414 of the body and the head 410. In the illustrated embodiment, the articulating member 416 articulates in at least four directions (up, down, right and left). In a variation, the articulating member 416 articulates in at least two directions. In a variation, the articulating member 416 is omitted and the shaft 406 is rigid and does not articulate.

The handle 404 includes a first actuator 418 and a second actuator 420. The first actuator 418 actuates the articulating member 416 to control up/down movement of the head 410. The second actuator 420 actuates the articulating member 416 to control left/right movement of the head 410. An example of such a probe is the I12C4f 4-way laparoscopic probe, a product of B-K Medical ApS, a company of Herlev, Denmark, which is a wholly owned subsidiary of Analogic Corporation, a company of MA, USA. Other laparoscopic probes are also contemplated herein. FIGS. 7 and 8 schematically illustrate the transducer array 112 and the tracking sensor(s) 116 and routing of wires 308 and 310 from inside of the head 410 through inside of the body 408 and the handle 404 to inside of the cable 120; the transducer array 112, the tracking sensor(s) 116 and the wires 308 and 310 are housed inside of the probe 402.

In FIGS. 7 and 8, the mechanism for articulating the articulating member 416 is omitted for sake of clarity. An example approach for articulating a head of a transducer probe is described in patent application Ser. No. 14/232,034, published as US 2014/0133269 A1, filed Jul. 12, 2011, and entitled "Ultrasound Imaging Probe," and patent application Ser. No. 14/760,550, published as US 2015/0335312 A1, filed Jan. 14, 2013, and entitled "Ultrasound Imaging Probe, and patent application Ser. No. 14/232,034, published as US 2014/0133269 A1, filed Jul. 12, 2011, and entitled "Ultrasound Imaging Probe," which are incorporated herein by reference in their entireties.

Figure 9:
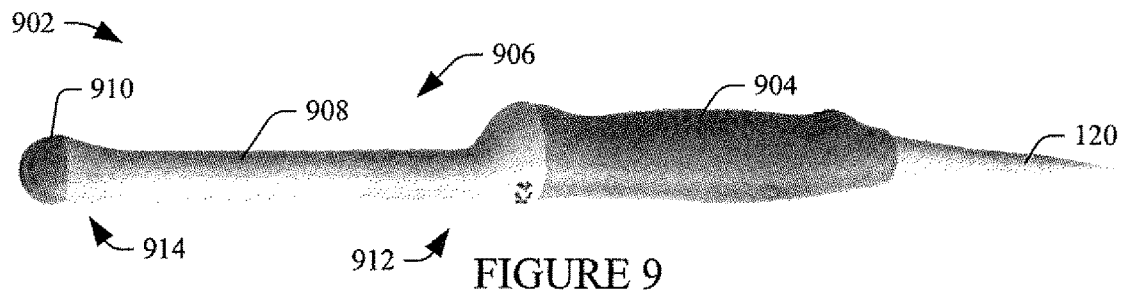
FIG. 9 illustrates an example endocavitary probe.
Figure 10:
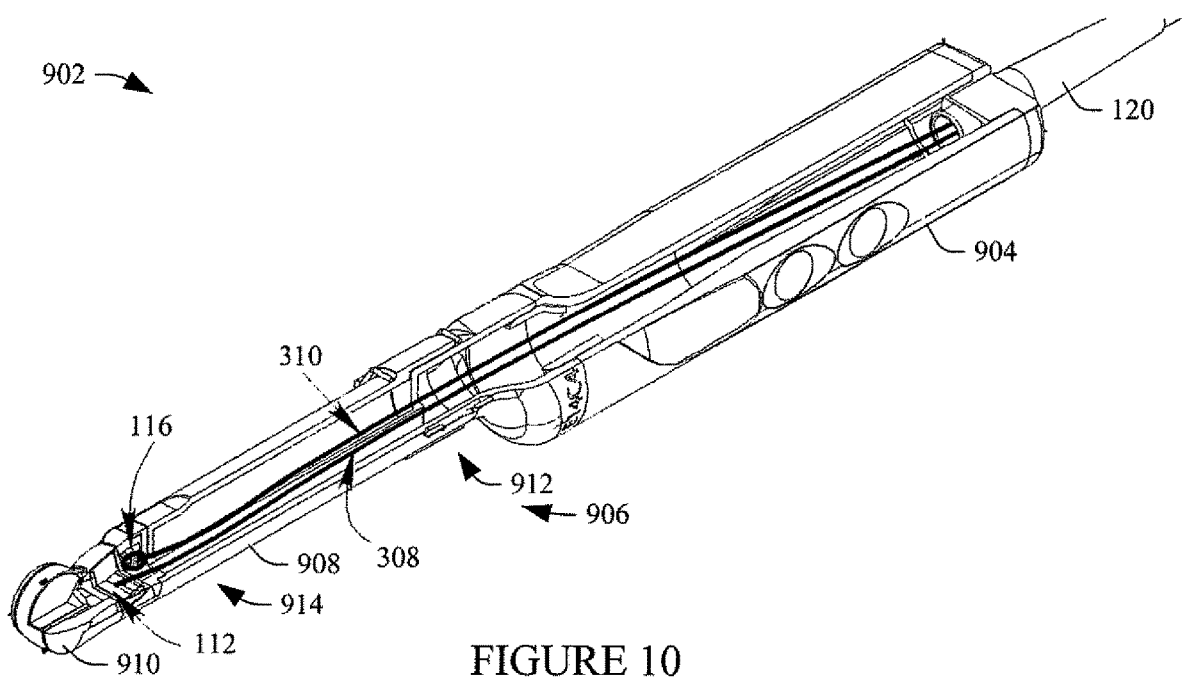
FIG. 10 illustrates example of the probe of FIG. 8 with a cut-away showing example sensor placement and routing of a wire therefrom to the cable.

FIGS. 9 and 10 illustrate another example of the ultrasound imaging probe 104. FIG. 9 illustrates a side view of the probe 104, and FIG. 10 schematically illustrates a perspective view with a cut-out showing a portion of an inside of the probe 104. In this example, the probe 104 is configured as an endocavitary probe 902.

The endocavitary probe 902 includes a handle 904 and an elongate shaft 906 having a long axis. The elongate shaft 906 includes a body 908 and a head 910, both aligned along the long axis. The body 908 includes a first end 912 and a second opposing end 914. The first end 912 of the body is affixed to the handle 904. FIGS. 9 and 10 also schematically illustrate the transducer array 112 and the tracking sensor(s) 116 and routing of the wires 308 and 310, respectively therefrom, from inside of the head 910 through inside of the body 908 of the shaft 906 and the handle 904 to the cable 120; the transducer array 112, the tracking sensor(s) 116 and the wires 308 and 310 are housed inside of the probe 902.

An example of such a probe is the E10C4 Endocavitary probe, a product of B-K Medical ApS, a company of Herlev, Denmark, which is a wholly owned subsidiary of Analogic Corporation, a company of MA, USA. Another suitable probe is the E14CL4b Endocavitary Biplane probe, a product of B-K Medical ApS, which is a wholly owned subsidiary of Analogic Corporation, a company of MA, USA. The E14CL4b Endocavitary Biplane probe include two transducer arrays. An example of an endocavitary probe is described in patent application Ser. No. 12/225,488, U.S. Pat. No. 9,259,208 B1, filed Oct. 20, 2009, and entitled "Ultrasound Probe," which is incorporated herein by reference in its entirety. Other endocavitary probes are also contemplated herein.

The approached described herein includes integrating a tracking sensor(s) 116 in an ultrasound imaging probe 104 with the transducer array 112, routing signals from both through the same single cable 120 to the same single interface 108, which is configured to connect to the complementary same single interface 110 of the console 106, which transmits at least ultrasound signals and sensor signals via the connection therebetween to the console 106. In one instance, this mitigates the complexity of attaching a sensor(s) 116 to the ultrasound probe 104, connecting the sensor(s) 116, managing two cables, connecting the magnetic field generator 142, interconnecting the tracking and the ultrasound system 136 and 102, configuring the system 102, calibration or registration, etc. associated with a configuration in which the same single cable 120 and the same single interface 108 are not utilized. By fully integrating the sensor(s) 116 in the ultrasound probe 104, the handling of it is completely taken out of the complexity.

Figure 11:
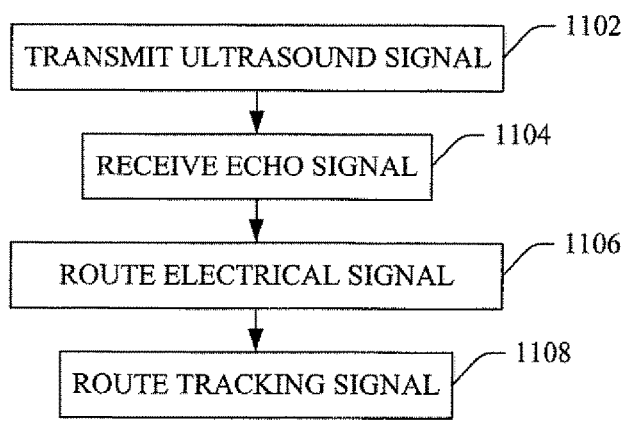
FIG. 11 illustrates an example method in accordance with an embodiment herein.

FIG. 11 illustrates a method in accordance with an embodiment described herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 1102, transmit an ultrasound signal with the transducer array 112.

At 1104, receive an echo signal with the transducer array 112.

At 1106, route the electrical signal indicative of the echo signal to the console 106 via the set of conductive members or elements 308, the connectors 108 and 110 and the cable 120

At 1108, route the tracking signal to the console 106 via the set of conductive members or elements 310, the connectors 108 and 110 and the cable 120.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound probe, comprising:
    an elongate shaft with a first end, a second end, and an elongate mid-portion between the first end and the second end;
    a head disposed at the first end, wherein the head encloses:
        a transducer array with a first electrical connection; and
        a tracking sensor with a second electrical connection;
    a handle with a third end and a fourth end, wherein the third end is coupled to the second end of the elongate shaft;
    a cable with a fifth end and a sixth end, wherein the fifth end is coupled to the fourth end of the handle;
    an electro-mechanical connector at the sixth end of the cable, wherein the electro-mechanical connector houses a circuit board;
    a first electrically conductive element with a seventh end and an eighth end, wherein the first electrically conductive element extends inside of the probe from the transducer array in the head respectively through the shaft, the handle and the cable to the circuit board in the electro-mechanical connector, wherein the seventh end is in electrical and mechanical communication with the first electrical connection of the transducer array, and the eighth end is in electrical and mechanical communication with the circuit board; and
    a second electrically conductive element with a ninth end and a tenth end, wherein the second electrically conductive element extends inside of the probe from the tracking sensor in the head respectively through the shaft, the handle and the cable to the circuit board in the electro-mechanical connector, wherein the ninth end is in electrical and mechanical communication with the second electrical connection of the tracking sensor, and the tenth end is in electrical and mechanical communication with the circuit board;
    wherein the electro-mechanical connector includes a set of pins and the circuit board is in electrical communication with the set of pins; and
    wherein the circuit board includes electronics that cycle through receiving a transmit pulse, transferring an electrical signal from the transducer array, and transferring a tracking signal from the tracking sensor, alternately using the same set of pins.

2. The ultrasound probe of claim 1, wherein the electronics gate the signals.

3. The ultrasound probe of claim 1, wherein the electronics includes circuitry configured to convert an analogic signal into a digital tracking signal.

4. The ultrasound probe of claim 1, wherein the set of pins includes a supply voltage pin, two differential signal pins, a clock pin, a select enable pin, a master output pin, a master input pin, and an interrupt pin.

5. The ultrasound probe of claim 1, wherein the tracking sensor is disposed proximate to the transducer array.

6. The ultrasound probe of claim 1, wherein the tracking sensor is disposed distal to the transducer array.

7. The ultrasound probe of claim 1, wherein the tracking sensor is integrated with the transducer array.

8. The ultrasound probe of claim 1, wherein the first end of the elongate shaft, including a portion thereof physically supporting the tracking sensor and the transducer array, is configured to articulate relative to the elongate mid-portion.

9. The ultrasound probe of claim 8, further including:
    a first actuator configured to control movement of the head in a first direction; and
    a second actuator configured to control movement of the head in a second different direction.

10. The ultrasound probe of claim 9, wherein the first and second directions are perpendicular to each.

11. The ultrasound probe of claim 8, wherein the ultrasound probe is configured as a laparoscopic ultrasound probe.

12. The ultrasound probe of claim 1, wherein the first end of the elongate shaft, including a portion thereof physically supporting the tracking sensor and the transducer array, is not capable of articulating relative to the elongate mid-portion.

13. The ultrasound probe of claim 1, further including a control configured to control the transducer array.

14. The ultrasound probe of claim 1, wherein the ultrasound probe is configured as an endo-cavitary probe.

15. The ultrasound probe of claim 3, wherein the conversion includes reducing an amount of data.

16. The ultrasound probe of claim 1, wherein the electromechanical connector includes a set of pins, wherein the circuit board is electrically connected between the pins and the first and second electrically conductive elements, and routes signals between the pins and the first and second electrically conductive elements.

17. The ultrasound probe of claim 1, wherein the circuit board is configured to route control signals.

18. The ultrasound probe of claim 1, wherein the circuit board is configured to route power signals.

* * * * *